United States Patent
Sueoka et al.

(10) Patent No.: US 9,964,617 B2
(45) Date of Patent: May 8, 2018

(54) MAGNETIC RESONANCE IMAGING APPARATUS, MAGNETIC RESONANCE IMAGING METHOD AND MEDICAL SYSTEM

(71) Applicant: Toshiba Medical Systems Corporation, Otawara-shi, Tochigi (JP)

(72) Inventors: Kazuhiro Sueoka, Nasushiobara (JP); Hideyuki Ooba, Nasushiobara (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 1330 days.

(21) Appl. No.: 13/742,549

(22) Filed: Jan. 16, 2013

(65) Prior Publication Data

US 2013/0147480 A1  Jun. 13, 2013

(30) Foreign Application Priority Data

Apr. 22, 2011 (JP) ................................. 2011-096637

(51) Int. Cl.
*G01R 33/54* (2006.01)
*A61B 5/055* (2006.01)
*G01R 33/483* (2006.01)

(52) U.S. Cl.
CPC ............ *G01R 33/543* (2013.01); *A61B 5/055* (2013.01); *G01R 33/4835* (2013.01)

(58) Field of Classification Search
CPC .... G01R 33/543; G01R 33/4835; A61B 5/055
USPC ....................................................... 324/309
See application file for complete search history.

(56) References Cited

U.S. PATENT DOCUMENTS

2007/0238963 A1   10/2007 Kaminaga et al.

FOREIGN PATENT DOCUMENTS

| JP | 3-118707 | 12/1991 |
|---|---|---|
| JP | 1991-118707 | 12/1991 |
| JP | 06-086770 | 3/1994 |
| JP | 2007-167634 | 7/2007 |

(Continued)

OTHER PUBLICATIONS

Japanese Patent 2007167634 A-machine translation Titile: Medical Image Diagnostic System, Server for Image Storage and Comminication System, Image Reference Device, and Medical Image Diagnostic System Publication date: Jul. 5, 2007, Inventor: Shigeo et al.*

(Continued)

*Primary Examiner* — Dixomara Vargas
(74) *Attorney, Agent, or Firm* — Nixon & Vanderhye P.C.

(57) ABSTRACT

According to one embodiment, a magnetic resonance imaging apparatus includes an imaging condition setting unit and an imaging unit. The imaging condition setting unit is configured to set slice positions same as past slice positions to a same object and to set a table position of a bed with the object set to position a position representing a slice position designated out of the slice positions or a position representing a slice range designated out of the slice positions on a center of a magnetic field. The imaging unit is configured to acquire magnetic resonance data from the slice positions set for the object at the table position of the bed to generate image data corresponding to the slice positions based on the acquired magnetic resonance data.

16 Claims, 10 Drawing Sheets

(56) References Cited

FOREIGN PATENT DOCUMENTS

| JP | 2008-148901 | 7/2008 |
|----|-------------|--------|
| JP | 2009-279218 | 12/2009 |
| JP | 2010-136824 | 6/2010 |
| WO | WO 2009/072619 | 6/2009 |

OTHER PUBLICATIONS

Japanese Patent 2008148901 A-machine translation Title: Magnetic Resonance Imaging Apparatus Publication date: Jul. 3, 2008 Inventor: Ono, Yoshiharu.*
Office Action dated May 23, 2014 in CN Patent Application No. 201280000415.8.
Office Action dated Apr. 3, 2015 in CN Patent Application No. 201280000415.8.
Office Action dated Mar. 29, 2016 in JP Patent Application No. 2012-087974.
Notification of Transmittal of Translation of the International Preliminary Report on Patentability in PCT/JP2012/059605 dated Oct. 31, 2013.
International Search Report for PCT/JP2012/059605, dated May 15, 2012.

* cited by examiner (A) PAST SLICE POSITIONS (B) CURRENT SLICE POSITIONS (A) PAST SLICE POSITIONS (B) CURRENT SLICE POSITIONS (A) PAST SLICE POSITIONS (B) CURRENT SLICE POSITIONS (A) PAST SLICE POSITIONS (B) CURRENT SLICE POSITIONS (A) PAST SLICE POSITIONS (B) CURRENT SLICE POSITIONS

MAGNETIC RESONANCE IMAGING APPARATUS, MAGNETIC RESONANCE IMAGING METHOD AND MEDICAL SYSTEM

CROSS REFERENCES TO RELATED APPLICATIONS

This is a continuation of Application PCT/JP2012/059605, filed Apr. 6, 2012.

This application is based upon and claims the benefit of priority from Japanese Patent Application No. 2011-096637, filed Apr. 22, 2011; the entire contents of which are incorporated herein by reference.

FIELD

Embodiments described herein relate generally to a MRI (magnetic resonance imaging) apparatus, a magnetic resonance imaging method and a medical system.

BACKGROUND

MRI is an imaging method which excites nuclear spins of an object set m a static magnetic field with a magnetic field RF (radio frequency) signal having the Larmor frequency and reconstructs an image based on NMR (NMR: nuclear magnetic resonance) signals generated due to the excitation.

In an MRI examination, image data is often acquired from an area that is the same as that used for acquisition of image data in the past. Specifically acquisition conditions of image data are set with reference to imaging conditions of image data acquired in the past. More specifically, the same imaging conditions, including a slice thickness, the number of slices and a slice angle, as past conditions can be set for imaging assuming that a position of an object is constant in an apparatus coordinate system.

[Prior Technical Literature]
[Patent literature 1] JPA 2007-167634

In an MRI apparatus, uniformity in the magnetic field decreases at a position further from the center of the static magnetic field. Therefore, there is a problem that an image data quality at a slice position far from the magnetic field center may be deteriorated. Especially, if a part of the highest interest is far from the magnetic field center in a case of acquiring image data repeatedly from a same imaging area, image data having a deteriorated image quality is acquired repeatedly because the same imaging area is repeatedly set constantly.

It is an object of the present invention to provide a magnetic resonance imaging apparatus, a magnetic resonance imaging method and a medical system which can acquire image data of a part of high interest repeatedly with an improved image quality.

DETAILED DESCRIPTION

In general, according to one embodiment, a magnetic resonance imaging apparatus includes an imaging condition setting unit and an imaging unit. The imaging condition setting unit is configured to set slice positions same as past slice positions to a same object and to set a table position of a bed with the object set to position a position representing a slice position designated out of the slice positions or a position representing a slice range designated out of the slice positions on a center of a magnetic field. The imaging unit is configured to acquire magnetic resonance data from the slice positions set for the object at the table position of the bed to generate image data corresponding to the slice positions based on the acquired magnetic resonance data.

In addition, a medical system according to an embodiment of the present invention includes a transmission request reception unit and a transmitting unit. The transmission request reception unit is configured to receive a transmission request of information from a magnetic resonance imaging apparatus. The information indicates slice positions set in a past for a designated object. The transmitting unit is configured to transmit information indicating a slice position designated out of the slice positions or information indicating a slice range designated out of the slice positions, together with the information indicating the slice positions, to the magnetic resonance imaging apparatus, as a response to the transmission request.

In addition, a magnetic resonance imaging method according to an embodiment of the present invention includes: setting slice positions same as past slice positions to a same object and setting a table position of a bed with the object set to position a position representing a slice position designated out of the slice positions or a position representing a slice range designated out of the slice positions on a center of a magnetic field; and acquiring magnetic resonance data from the slice positions set for the object at the table position of the bed to generate image data corresponding to the slice positions based on the acquired magnetic resonance data.

A magnetic resonance imaging apparatus, a magnetic resonance imaging method and a medical system according to embodiments of the present invention will be described with reference to the accompanying drawings.

Figure 1:
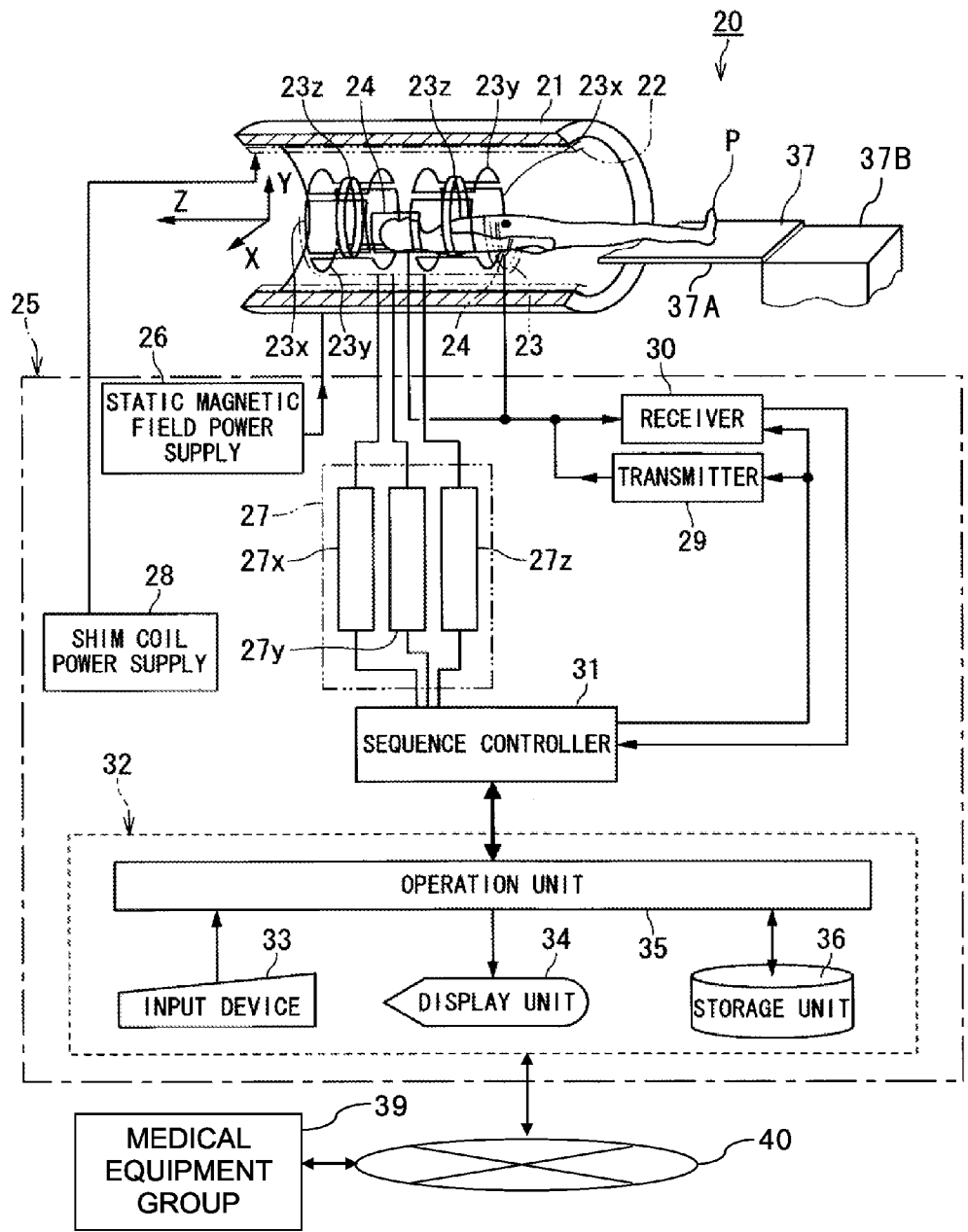
FIG. 1 is a block diagram showing a magnetic resonance imaging apparatus according to an embodiment of the present invention.

FIG. 1 is a block diagram showing a magnetic resonance imaging apparatus according to an embodiment of the present invention.

A magnetic resonance imaging apparatus 20 includes a static field magnet 21 for generating a static magnetic field, a shim coil 22 arranged inside the static field magnet 21 which is cylinder-shaped, a gradient coil 23 and RF coils 24.

The magnetic resonance imaging apparatus 20 also includes a control system 25. The control system 25 includes a static magnetic field power supply 26, a gradient power supply 27, a shim coil power supply 28, a transmitter 29, a receiver 30, a sequence controller 31 and a computer 32. The gradient power supply 27 of the control system 25 includes an X-axis gradient power supply 27x, a Y-axis gradient power supply 27y and a Z-axis gradient power supply 27z. The computer 32 includes an input device 33, a display unit 34, an operation unit 35 and a storage unit 36.

The static field magnet 21 communicates with the static magnetic field power supply 26. The static magnetic field power supply 26 supplies electric current to the static field magnet 21 to get the function to generate a static magnetic field in an imaging region. The static field magnet 21 includes a superconductivity coil in many cases. The static field magnet 21 gets current from the static magnetic field power supply 26 which communicates with the static field magnet 21 at excitation. However, once excitation has been made, the static field magnet 21 is usually isolated from the static magnetic field power supply 26. The static field magnet 21 may include a permanent magnet which makes the static magnetic field power supply 26 unnecessary.

The static field magnet 21 has the cylinder-shaped shim coil 22 coaxially inside itself. The shim coil 22 communicates with the shim coil power supply 28. The shim coil power supply 28 supplies current to the shim coil 22 so that the static magnetic field becomes uniform.

The gradient coil 23 includes an X-axis gradient coil 23x, a Y-axis gradient coil 23y and a Z-axis gradient coil 23z. Each of the X-axis gradient coil 23x, the Y-axis gradient coil 23y and the Z-axis gradient coil 23z which is cylinder-shaped is arranged inside the static field magnet 21. The gradient coil 23 has also a bed 37 in the area formed inside it which is an imaging area. The bed 37 supports an object P. The RF coils 24 include a whole body coil (WBC: whole body coil), which is built in the gantry, for transmission and reception of RF signals and local coils, which are arranged around the bed 37 or the object P, for reception of RF signals.

The gradient coil 23 communicates with the gradient power supply 27. The X-axis gradient coil 23x, the Y-axis gradient coil 23y and the Z-axis gradient coil 23z of the gradient coil 23 communicate with the X-axis gradient power supply 27x, the Y-axis gradient power supply 27y and the Z-axis gradient power supply 27z of the gradient power supply 27 respectively.

The X-axis gradient power supply 27x, the Y-axis gradient power supply 27y and the Z-axis gradient power supply 27z supply currents to the X-axis gradient coil 23x, the Y-axis gradient coil 23y and the Z-axis gradient coil 23z respectively so as to generate gradient magnetic fields Gx, Gy and Gz in the X, Y and Z directions in the imaging area.

The RF coils 24 communicate with the transmitter 29 and/or the receiver 30. The transmission RF coil 24 has a function to transmit a RF signal given from the transmitter 29 to the object P. The reception RF coil 24 has a function to receive NMR signals generated due to a nuclear spin inside the object P which is excited by the RF signal to give to the receiver 30.

The sequence controller 31 of the control system 25 communicates with the gradient power supply 27, the transmitter 29 and the receiver 30. The sequence controller 31 has a function to storage sequence information describing control information needed in order to make the gradient power supply 27, the transmitter 29 and the receiver 30 drive and generate gradient magnetic fields Gx, Gy and Gz in the X, Y and Z directions and a RF signal by driving the gradient power supply 27, the transmitter 29 and the receiver 30 according to a predetermined sequence stored. The control information above-described includes motion control information, such as intensity, impression period and impression timing of the pulse electric current which should be impressed to the gradient power supply 27.

The sequence controller 31 is also configured to give raw data to the computer 32. The raw data is complex data obtained through the detection of a MR signal and A/D (analog to digital) conversion to the NMR signal detected in the receiver 30.

The transmitter 29 has a function to give a RF signal to the RF coil 24 in accordance with control information provided from the sequence controller 31. The receiver 30 has a function to generate raw data which is digitized complex number data by detecting an NMR signal given from the RF coil 24 and performing predetermined signal processing and A/D converting to the NMR signal detected. The receiver 30 also has a function to give the generated raw data to the sequence controller 31.

In addition, an ECG (electro cardiogram) unit for acquiring an ECG signal of the object P is provided with the magnetic resonance imaging apparatus 20, as needed. The ECG signal detected by the ECG unit is outputted to the computer 32 through the sequence controller 31.

Note that, a PPG (peripheral pulse gating) signal representing a beat as pulse wave information may be acquired instead of an ECG signal representing a beat as heart rate information. A PPG signal is acquired by detecting a pulse wave of e.g. tip of a finger as an optical signal. When a PPG signal is acquired, a PPG signal detection unit is provided with the magnetic resonance imaging apparatus 20.

Furthermore, the bed 37 includes a table 37A and a bed driving unit 37B. The bed driving unit 37B is connected to the computer 32 through the sequence controller 31. Then, the bed driving unit 37B is configured to perform positioning of the table 37A under the control of the sequence controller 31 based on imaging conditions set by the computer 32.

Furthermore, imaging by the stepping-table method can be also performed with moving the table 37A of the bed 37. The stepping-table method is the imaging technique with moving the table 37A of the bed 37 step by step for each station. The stepping-table method is used for imaging of a wide area which cannot be completed once like whole body imaging. The images acquired with moving the table 37A can be stitched with each other by stitching processing in the computer 32.

On the other hand, the computer 32 is connected with a medical equipment group 39 including a medical information management system, a medical image server, a medical image processing apparatus, a medical image display apparatus and other image diagnostic apparatuses through the network 40. The network 40 can be not only a LAN (Local Area Network) like an in-hospital network in a certain medical institution but also the internet or a special wide area network used between plural medical institutions. Connecting the magnetic resonance imaging apparatus 20 with a medical equipment placed in another medical institution can achieve a remote medical care using the magnetic resonance imaging apparatus 20.

The computer 32 gets various functions by the operation unit 35 executing some programs stored in the storage unit 36 of the computer 32. Alternatively, some specific circuits having various functions may be provided with the magnetic resonance imaging apparatus 20 instead of at least a part of the programs.

Figure 2:
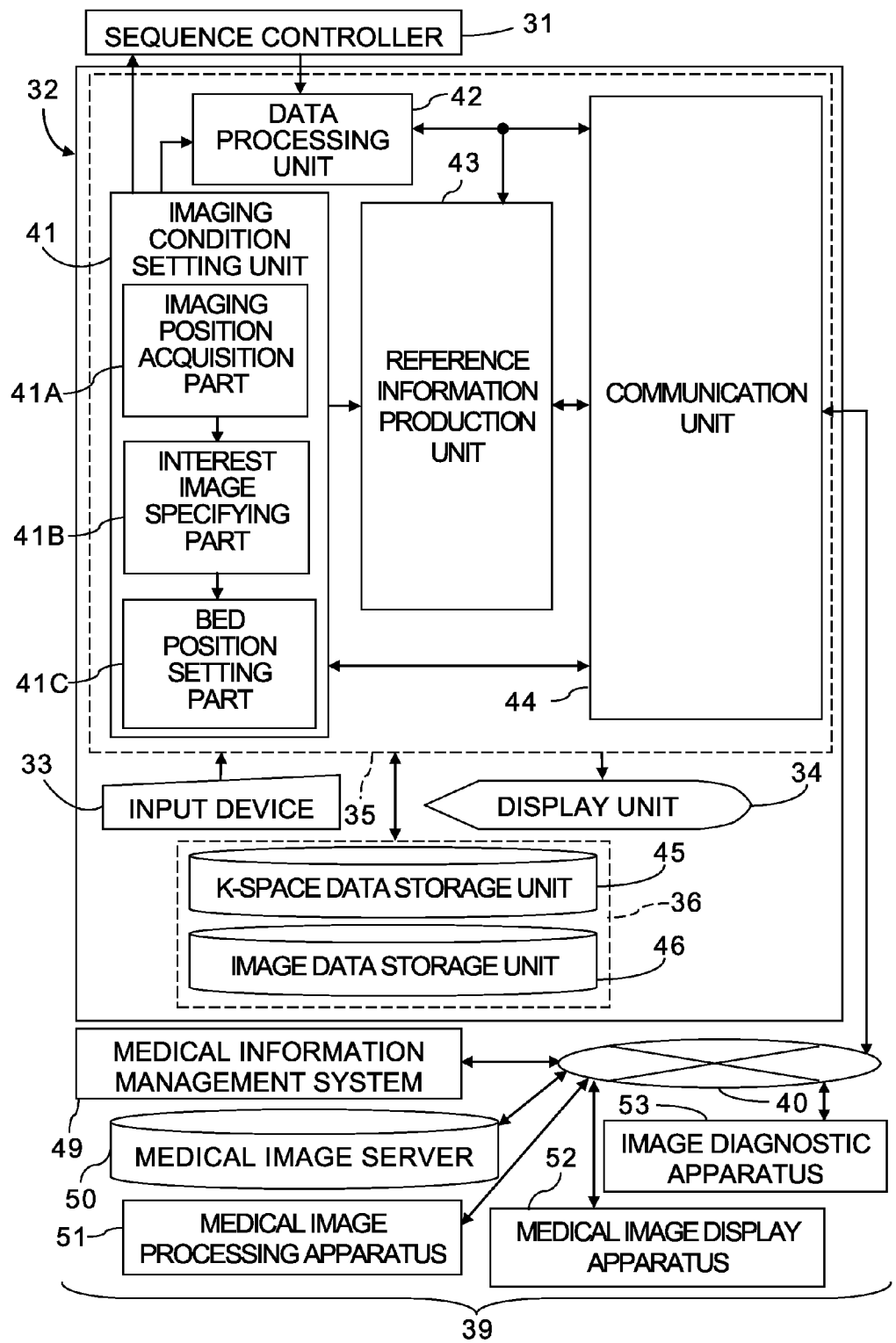
FIG. 2 is a block diagram showing functions of the computer and a detailed configuration of the medical the medical equipment group shown in FIG. 1.

FIG. 2 is a block diagram showing functions of the computer 32 and a detailed configuration of the medical the medical equipment group 39 shown in FIG. 1.

The operation unit 35 of the computer 32 functions as an imaging condition setting unit 41, a data processing unit 42, a reference information production unit 43 and a communication unit 44 by executing the programs stored in the storage unit 36. The imaging condition setting unit 41 has an imaging position acquisition part 41A, an interest image specifying part 41B and a bed position setting part 41C. Furthermore, the storage unit 36 functions as a k-space data storage unit 45 and an image data storage unit 46.

On the other hand, each of the medical information management system 49, the medical image server 50, the medical image processing apparatus 51, the medical image display apparatus 52 and another image diagnostic apparatus 53 consisting of the medical equipment group 39 is connected with the computer 32 through the network 40. Examples of the image diagnostic apparatus 53 include another magnetic resonance imaging apparatus, an X-ray CT (computed tomography) apparatus and a PET (positron emission computed tomography) apparatus.

The medical information management system 49 is a system such as a RIS (Radiology Information System) or a HIS (Hospital Information System) for managing examination order information including information designating imaging conditions, such as an imaging part, and patient information, such as identification information of a patient.

The medical image server 50 is an image data management system such as a PACS (Picture archiving And Communication System) for storing medical image data as image data of the DICOM (Digital Imaging and Communication in Medicine) protocol which is a transmission protocol of medical image data.

The medical image processing apparatus 51 is an apparatus having image processing function of image data of the DICOM protocol acquired from a transmission source like the medical image server 50 through the network 40. The medical image processing apparatus 51 can be configured by a computer system like a work station.

In the medical image processing apparatus 51, a frame or frames of slice image data of interest can be designated from frames of slice image data as key image data. Then, marking information indicating correspondence with the key image data, a slice position of a key image in a body coordinate system fixed on an object P and a distance from the center of magnetic field of the magnetic resonance imaging apparatus 20 to a slice position corresponding to a key image can be attached to each designated frame of slice image data as key image information. That is, the key image information can be attached to image data of the DICOM protocol as tag information.

Each slice position of key images can be obtained based on coordinate information included in slice image data.

Furthermore, a distance from the center of magnetic field to each of slice positions corresponding to key images can be expressed by using the apparatus coordinate system fixed with the static field magnet 21 of the magnetic resonance imaging apparatus 20. The apparatus coordinate system can be defined by setting the central axis direction of the static field magnet 21 as the z-axis, the horizontal direction orthogonal to the central axis of the static field magnet 21 as the x-axis and the vertical direction as the y-axis. Then, the origin (x, y, z)=(0, 0, 0) of the apparatus coordinate system can be set to the center of magnetic field.

Therefore, by using the apparatus coordinate system of which origin is the center of magnetic field in the static field magnet 21, a distance from the center of magnetic field to each of slice positions corresponding to key images can be obtained as a coordinate value of the slice position expressed by the apparatus coordinate system.

The medical image display apparatus 52 is an image viewer displaying image data of the DICOM protocol acquired from a transmission source like the medical image server 50 through the network 40. The medical image display apparatus 52 has a simple image processing function and a function to generate an interpretation report with reference to medical image data.

Especially, the medical image display apparatus 52 has a function to generate interpretation report information linked with medical image data of interest stored in a storage unit like the medical image server 50. For that purpose, in the medical image display apparatus 52, a frame or frames of slice image data of interest can be also designated from frames of slice image data as key image data. Then, key image information, including marking information, a slice position and a distance from the center of magnetic field, of a key image can be attached to each designated frame of slice image data.

The imaging condition setting unit 41 of the computer 32 has a function to acquire examination order information, transmitted from the medical information management system 49 via the network 40, through the communication unit 44 to perform processing for registering a patient based on the patient information included in the acquired examination order information. The imaging condition setting unit 41 also has a function to set imaging conditions, including a pulse sequence, imaging slice positions and positioning information of the table 37A of the bed 37, based on information designating the imaging conditions included in the examination order information and instructing information from the input device 33; and a function to output the set imaging conditions to the sequence controller 31.

Especially, the imaging condition setting unit 41 has a function to set imaging slice positions, same as imaging slice positions set for a same object P as a past imaging condition, as a new imaging condition. The imaging condition setting unit 41 also has a function to set a control position of the table 37A to an appropriate position for the center of magnetic field, such as a position at which a single or multiple imaging slice positions designated as a key image position or key image positions of high interest become as close to the center of magnetic field in the static field magnet 21 as possible in a case of setting the same imaging slice positions as those in the past for an object P.

Specifically, the imaging condition setting unit 41 has a function to adjust positions of a set of slices in the apparatus coordinate system fixed with the center of magnetic field in the static field magnet 21 to set the positions of the slice set as a control condition of a position of the table 37A without changing positions of the set of slices set for an object P using a body coordinate system fixed with the object P.

The imaging position acquisition part 41A has a function to acquire position information of imaging slices set for a same object P, as a past imaging condition, by using a body coordinate system. The information specifying slice positions set in the past can be stored in an arbitrary apparatus of the medical equipment group 39. Therefore, the imaging position acquisition part 41A has a function to retrieve and acquire past slice position information, corresponding to patient information subjected to registration processing, from the medical equipment group 39 through the network 40, according to instructing information from the input device 33.

On the contrary, each medical system like the medical image processing apparatus 51 consisting of the medical equipment group 39 can have necessary functions in order to respond to a request from the imaging position acquisition part 41A. Specifically, each medical system can have a function as a transmission request reception unit receiving a transmission request of information, indicating slice positions set in the past for a designated object P, from the magnetic resonance imaging apparatus 20. Each medical system can also have a function as a transmission unit transmitting information indicating slice positions designated as key image positions of high interest among slice positions or information indicating a slice range designated as key image positions among the slice positions, together with information indicating the slice positions, to the magnetic resonance imaging apparatus 20, as a response to the transmission request.

The slice position information set by using a body coordinate system can be attached to each piece of diagnostic image data of the DICOM protocol as tag information. However, desired information such as imaging condition information including the slice positions information can be stored and managed as image data of the DICOM protocol, separately from diagnostic image data. Therefore, past slice position information can be acquired by referring to the tag information attached to image data of the DICOM protocol corresponding to the object P.

Furthermore, the past slice position information or image data with the past slice position information attached can be also stored in the image data storage unit 46 of the magnetic resonance imaging apparatus 20. Therefore, the imaging position acquisition part 41A may acquire the past slice position information with reference to the image data storage unit 46.

The interest image specifying part 41B has a function to acquire key image information, including marking information, slice positions and distances from the center of magnetic field, of key images of high interest from past image data with the key image information attached to specify slice positions, in a body coordinate system, corresponding to the key images, out of the slice positions acquired by the imaging position acquisition part 41A.

Furthermore, the interest image specifying part 41B is configured to designate a frame or frames of slice image data of interest as key image data from frames of past slice image data to specify slice positions of the designated key image data when any frame of the past slice image data is not designated as the key image data.

The designation of the key image data can be performed manually according to designating information of key images input to the interest image specifying part 41B from the input device 33. Furthermore, the interest image specifying part 41B may acquire reference information like setting information of a ROI (region of interest) from desired medical equipment through the network 40 to designate the key image data automatically based on the acquired reference information.

The bed position setting part 41C has a function to set an appropriate control position of the table 37A so as to make a frame or frames of slice positions corresponding to the key image or the key images as close to the center of magnetic field as possible. The bed position setting part 41C also has a function to correct the set control position of the table 37A so that the slice positions to be imaging targets become within a predetermined range from the center of magnetic field based on instructing information from the input device 33.

When a slice position corresponding to a single key image has been designated, the control position of the table 37A can be set so that the designated slice position becomes the closest position to the center of magnetic field.

On the other hand, when slice positions corresponding to equally or unequally spaced key images have been designated, the control position of the table 37A can be set so that the position, such as the center position or the barycentric position, representing the designated slice positions becomes the closest position to the center of magnetic field. The position representing the slice positions can be set automatically according to a desired algorithm determined in advance by the bed position setting part 41C. Further, the position representing the slice positions may be set manually based on instructing information from the input device 33.

Alternatively, when slice positions corresponding to key images have been designated, the control position of the table 37A can be set so that the range of the slices becomes within a predetermined range from the center of magnetic field. For example, a predetermined range to include a range of slices can be set to the FOV (Field of View) in which ununiformity of the static magnetic field is small. However, an area, close to the center of magnetic field, other than the FOV, may be a predetermined range which should include a range of slices.

Furthermore, when the designated slice position or slice positions are a section or sections, like the axial section or the axial sections, of which normal direction is the moving direction of the table 37A, the control position of the table 37A can be set so that the designated slice position or the representative position of the designated slice positions becomes the center of magnetic field. Therefore, if the table 37A can move in the vertical direction or in the horizontal direction perpendicular to the longitudinal direction, the control position of the table 37A can be set so that the designated slice position or the representative position of the designated slice positions becomes the center of magnetic field even though the designated slice position or slice positions are the coronal or sagittal section or sections.

Furthermore, when the designated slice position or slice positions are oblique section or sections, the control position of the table 37A can be set so as to make the designated slice position or the representative position of the designated slice positions be the closest position to the center of magnetic field, e.g., the position passing through the center of magnetic field.

In addition, the bed position setting part 41C has a function to determine whether the slice positions at the control position of the table 37A are within a predetermined range from the center of magnetic field, in order to correct the set control position of the table 37A. When the slice positions at the control position of the table 37A are not within the predetermined range from the center of magnetic field, the bed position setting part 41C is configured to display warning information showing that on the display unit 34. Furthermore, the bed position setting part 41C has a function to set the control position of the table 37A again according to instructing information input from the input device 33 when the warning information has been displayed.

In case of displaying the warning information, the bed position setting part 41C may display choices of reconfiguration methods on the display unit 34 and acquire select information of a choice as instructing information from the input device 33. For example, choices such as a choice for adjusting the control position of the table 37A manually and a choice for keeping the control position of the table 37A can be determined precedently and displayed.

The data processing unit 42 has a function to generate image data mainly based on raw data acquired from the sequence controller 31 and a function to output the generated image data.

The function for generating image data specifically consists of a function to receive raw data from the sequence controller 31 and store the raw data as k-space data in the k-space formed in the k-space data storage unit 4, a function to reconstruct image data by image reconstruction processing including the FT (Fourier transform) of the k-space data, a function to perform image processing necessary for image data, a function to acquire image processing conditions, which had been used for generation of past image data, for the image processing from the medical equipment group 39 through the network 40 and the communication unit 44, and the like.

The function for outputting image data specifically consists of a function to display image data on the display unit 34, a function to write image data in the image data storage unit 46, a function to have the communication unit 44 transmit image data of the DICOM protocol to a desired transmission destination of the medical equipment group 39 through the network 40, and the like.

Furthermore, the data processing unit 42 has a function to acquire imaging conditions like slice positions from the imaging condition setting unit 41 to attach them with corresponding image data as incidental information together with information specifying conditions for image processing having been performed for the image data; a function to designate a frame or frames of slice image data of interest, out of frames of slice image data, as key image data based on instructing information from the input device 33 to attach key image information, including marking information of key images, slice positions of key images and distances from the center of magnetic field to key images, with the designated slice image data; and a function to give the information specifying image processing conditions and the key image information to the reference information production unit 43.

The reference information production unit 43 has a function to generate information, such as imaging conditions like setting information of slice positions and/or the information specifying image processing conditions, to be shared as reference information in the medical equipment group 39, in the form of image data of the DICOM protocol. The reference information production unit 43 also has a function to transmit the generated image data of the DICOM protocol to a desired transmission destination of the medical equipment group 39 through the communication unit 44 via the network 40. For that purpose, the reference information production unit 43 is configured to be able to acquire necessary setting information of imaging conditions from the imaging condition setting unit 41 and necessary information specifying image processing conditions from the data processing unit 42 respectively.

Furthermore, the reference information production unit 43 is configured to attach key image information with the image data of the DICOM protocol, on which reference information such as imaging conditions and/or information specifying image processing conditions has been recorded, as tag information in the case where the key image information is acquired from the data processing unit 42.

Here, image data of the DICOM protocol recording the reference information is referred to as object data, distinctively from diagnostic image data of an object P. It is convenient to generate the object data as data made by attaching imaging conditions including respective slice positions and information specifying image processing conditions with positioning image data having been used for setting the slice positions. Accordingly, description is given hereinafter as an example case where the reference information production unit 43 generates object data including positioning image data with imaging conditions including respective slice positions and information specifying image processing conditions attached.

Therefore, each medical system, like the medical image processing apparatus 51, configuring the medical equipment group 39 can be also configured to transmit object data, made by attaching information indicating slice positions in addition to information indicating slice positions designated as key images among the slice positions or information indicating a slice range designated as key images among the slice positions with positioning image data as incidental information, to the magnetic resonance imaging apparatus 20.

The communication unit 44 has a function to communicate the computer 32 with each of the medical equipment group 39 through the network 40. Specifically, the communication unit 44 has a function to transmit and receive data, such as setting information of imaging conditions, diagnostic image data of the DICOM protocol, setting information of image processing conditions, and object data of the DICOM protocol, between a desired element of the medical equipment group 39 and each of the imaging condition setting unit 41, the data processing unit 42 and the reference information production unit 43 through the network 40.

Then, the operation and action of the magnetic resonance imaging apparatus 20 will be described.

Figure 3:
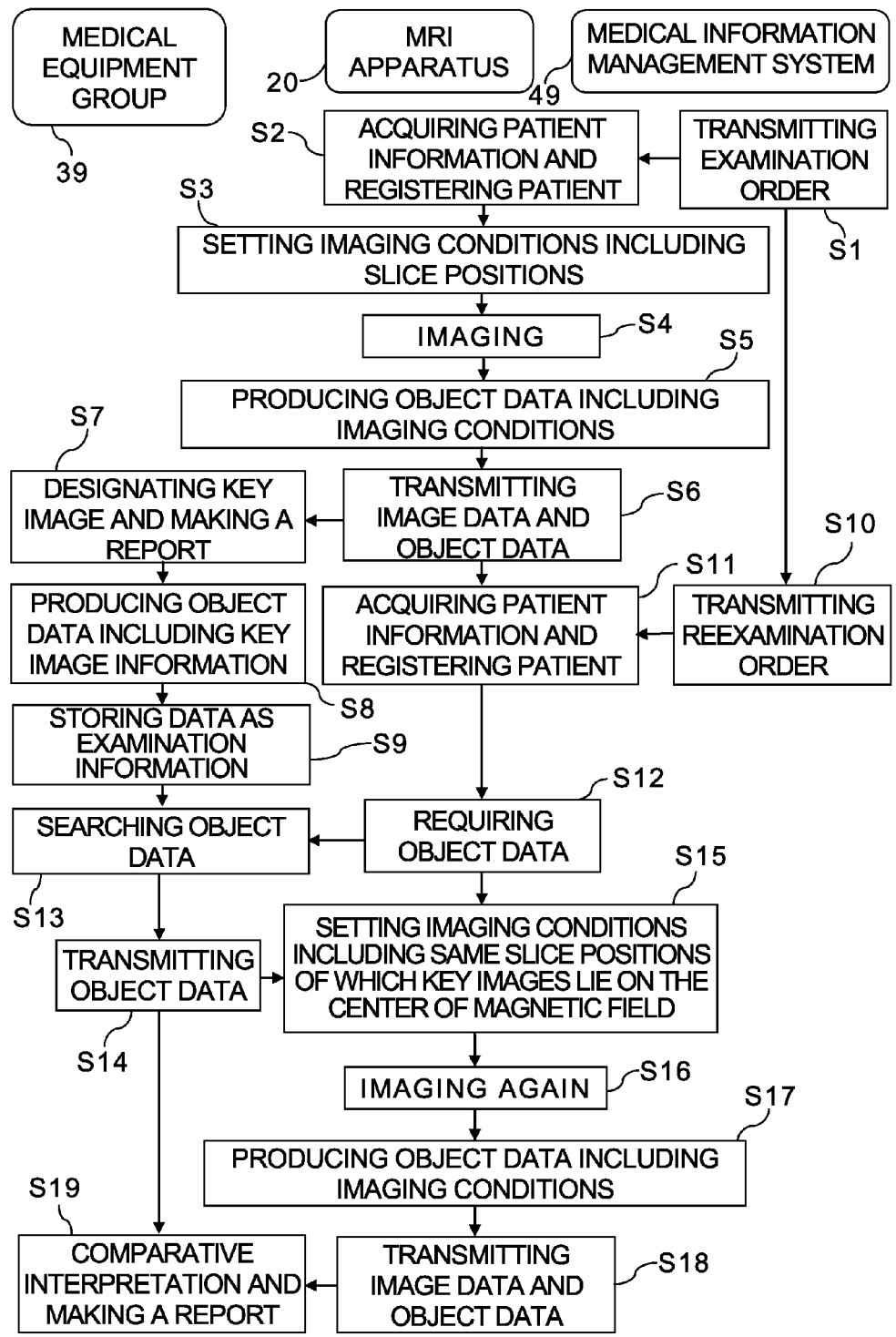
FIG. 3 is a flowchart showing a flow for performing imaging with regard to slice positions set to the object repeatedly with the magnetic resonance imaging apparatus shown in FIG. 1.

FIG. 3 is a flowchart showing a flow for performing imaging with regard to slice positions set to the object P repeatedly with the magnetic resonance imaging apparatus 20 shown in FIG. 1.

Firstly, in the step S1, examination order information is transmitted to the computer 32 of the magnetic resonance imaging apparatus 20 from the medical information management system 49 through the network 40.

Then, in the step S2, the communication unit 44 of the computer 32 receives the examination order information and gives it to the imaging condition setting unit 41. Subsequently, the imaging condition setting unit 41 acquires patient information included in the examination order information to perform a patient registration.

Meanwhile, the object P corresponding to the patient information is set to on the table 37A of the bed 37, and a static magnetic field is generated in an imaging area of static field magnet 21 excited by the static magnetic field power supply 26. Further, the shim-coil power supply 28 supplies current to the shim coil 22, thereby uniformizing the static magnetic field generated at the imaging area. Then, the bed driving unit 37B drives to send the table 37A, having the set object P, into the imaging area in the gantry in which the static field magnet 21 is built.

Next, in the step S3, the imaging condition setting unit 41 sets imaging conditions including slice positions. For that purpose, positioning image data referred to in order to set reference image data of an object P, such as orthogonal three cross section image data, and slice positions is acquired Then, slices to be imaging targets are set using a body coordinate system fixed with the object P by the operation of the input device 33 through positioning images, such as sagittal section images, coronal section images or axial section images, involving an imaging part and displayed on the display unit 34.

Next, the center position of the slice in the apparatus coordinate system fixed with the gantry and the static field magnet 21 is obtained so that the center of the slices set by using the body coordinate system lies on the center of magnetic field in the static field magnet 21. Then, the bed driving unit 37B is driven based on the center position of the slices in the apparatus coordinate system and the relative position relation between the body coordinate system and the apparatus coordinate system. Consequently, the table 37A is shifted with the object P and the body coordinate system so that the center of the slices lies on the center of magnetic field showing high uniformity in the magnetic field.

In addition, other imaging conditions including a pulse sequence are set in the imaging condition setting unit 41, in accordance with information specifying imaging conditions included in the examination order information and instructing information input from the input device 33. For example, imaging conditions including a delay time from an ECG signal are set when an ECG synchronized imaging is performed.

Next, in the step S4, the slices set to the object P are imaged in accordance with the set imaging conditions. Specifically, the imaging conditions are output from the imaging condition setting unit 41 to the sequence controller 31. Therefore, the sequence controller 31 drives the gradient power supply 27, the transmitter 29, and the receiver 30 in accordance with the imaging conditions, thereby generating a gradient magnetic field at the imaging area having the set object P, and further generating RF signals from the RF coil 24.

Consequently, the RF coil 24 receives NMR signals generated due to nuclear magnetic resonance in the object P. Then, the receiver 30 receives the NMR signals from the RF coil 24 and generates raw data which is digital data of NMR signals by A/D (analog to digital) conversion subsequently to necessary signal processing. The receiver 30 supplies the generated raw data to the sequence controller 31. The sequence controller 31 supplies the NMR signals as the raw data to the computer 32.

Then, the data processing unit 42 of the computer 32 arranges the NMR signals, acquired from the sequence controller 31, in the k-space formed in the k-space data storage unit 45 as k-space data. Next, the data processing unit 42 reconstructs frames of slice image data by image reconstruction processing of the k-space data acquired from each slice. In addition, necessary image processing is performed for each frame of the slice image data in the data processing unit 42 and slice mages for a diagnostic after the image processing are displayed on the display unit 34.

Furthermore, the data processing unit 42 attaches information specifying image processing conditions and imaging conditions including the slice positions acquired from the imaging condition setting unit 41 with corresponding frames of the slice image data as incidental information. Then, the data processing unit 42 writes and stores necessary slice image data in the image data storage unit 46.

Furthermore, the data processing unit 42 converts slice image data which should be stored in the medical image server 50 into image data of the DICOM protocol. In such case, the incidental information including the information specifying image processing conditions and the imaging conditions can be attached to each frame of the slice image data of the DICOM protocol as tag information.

Next, in the step S5, the reference information production unit 43 acquires the positioning image data used to set each slice position and the information specifying image processing conditions to the slice image data from the data processing unit 42 and the image conditions including information specifying each slice position from the imaging condition setting unit 41 respectively. Then, the reference information production unit 43 generates object data of the DICOM protocol consisting of the positioning image data and the attached imaging conditions, including the respective slice positions, and information specifying image processing conditions.

Next, in the step S6, the communication unit 44 transmits the object data generated in the reference information production unit 43 and the set of the image data, corresponding to the slice positions, generated in the data processing unit 42, to the medical image server 50 through the network 40.

Next, in the step S7, the medical image server 50 receives and stores the frames of slice image data and the object data. Then, a user can read the frames of slice image data and the object data from the medical image server 50 by a desired medical equipment such as the medical image processing apparatus 51 or the medical image display apparatus 52 to browse and edit the frames of slice image data and the object data.

For example, slice images can be displayed on the medical image display apparatus 52 and a single slice image or plural slice images of interest can be designated as key images by operating an input device included in the medical image display apparatus 52. Herewith, key image information including marking information of the key images, slice positions of the key images and distances from the center of magnetic field to the key images are attached as tag information with the slice image data designated as the key images. The distances from the center of magnetic field to the frames of key image data can be obtained based on coordinate information, in the apparatus coordinate system, attached with the slice image data, corresponding to the key images, as the tag information. Then, a diagnostic report can be made by quoting the designated key images.

Next, in the step S8, the key image information including the marking information of the key images, the slice positions of the key images and the distances from the center of magnetic field to the key images are attached to the object data in the medical image display apparatus 52. That is, object data including the key image information as the tag information is generated. Note that, the generation of the object data including the key image information may be performed in another medical equipment.

Next, in the step S9, the object data including the key image information and the set of the frames of the slice image data out of which the frames of key image data have the attached key image information are forwarded and stored as examination information to and in the medical image server 50. Generally, a set of frames of slice image data acquired by a multi slice scan and corresponding object data are stored and managed in the medical image server 50 as data which belongs to a common series.

Note that, a designation of key images and an attachment of key image information to slice image data can be performed by a function of the data processing unit 42 in the magnetic resonance imaging apparatus 20 as well as medical equipment out of the medical equipment group 39. In this case, object data including the key image information as incidental information can be generated by the reference information production unit 43 of the magnetic resonance imaging apparatus 20.

Then, according to a medical plan, an operation and a treatment of the object P can be performed. In addition, when it is required to acquire image data for a progress observation of the object P after a surgery of the object P or the like, a reexamination is performed by the magnetic resonance imaging apparatus 20.

In that case, in the step S10, reexamination order information is transmitted from the medical information management system 49 to the magnetic resonance imaging apparatus 20 through the network 40.

Therefore, in the step S11, the imaging condition setting unit 41 of the magnetic resonance imaging apparatus 20 acquires patient information included in the reexamination order information to perform a patient registration, similarly to the step S2.

Next, in the step S12, the imaging condition setting unit 41 transmits a transmission request of past examination information, corresponding to the patient information, to the medical image server 50 through the communication unit 44 and the network 40 since the order information is the reexamination order information. The past examination information may be slice image data itself or incidental information of slice image data. However, it is assumed that a transmission of highly convenient object data is required here.

Next, in the step S13, the medical image server 50 responds to the transmission request of the object data from the imaging condition setting unit 41 and searches past object data corresponding to the patient information.

Next, in the step S14, the medical image server 50 transmits the past object data, corresponding to the patient information, obtained as a result of the search, to the magnetic resonance imaging apparatus 20 through the network 40.

Next, in the step S15, imaging condition setting unit 41 acquires the past object data corresponding to the patient information from the medical image server 50 through the network 40 and the communication unit 44. Then, the imaging condition setting unit 41 refers to the past object data to set imaging conditions including a position of the table 37A in order to perform re-imaging for the same slice positions as those in the past with laying the slice positions of the key images on the center of magnetic field.

Note that, the imaging condition setting unit 41 may acquire past slice image data instead of the past object data to set imaging conditions for the re-imaging with reference to tag information attached to the past slice image data. Specifically, the imaging condition setting unit 41 can acquire slice positions or a slice range designated as key images, as a form of incidental information attached to arbitrary image data, of the DICOM communication protocol, received through the network 40. Then, imaging conditions with laying the acquired slice positions or slice range of the key images on the center of magnetic field can be set for the re-imaging.

Note that, a distance from the center of magnetic field to a position representing slice positions or a slice range designated as key images may be acquired as incidental information to set imaging conditions including a position of the table 37A, based on the acquired distance from the center of magnetic field, for the re-imaging.

Figure 4:
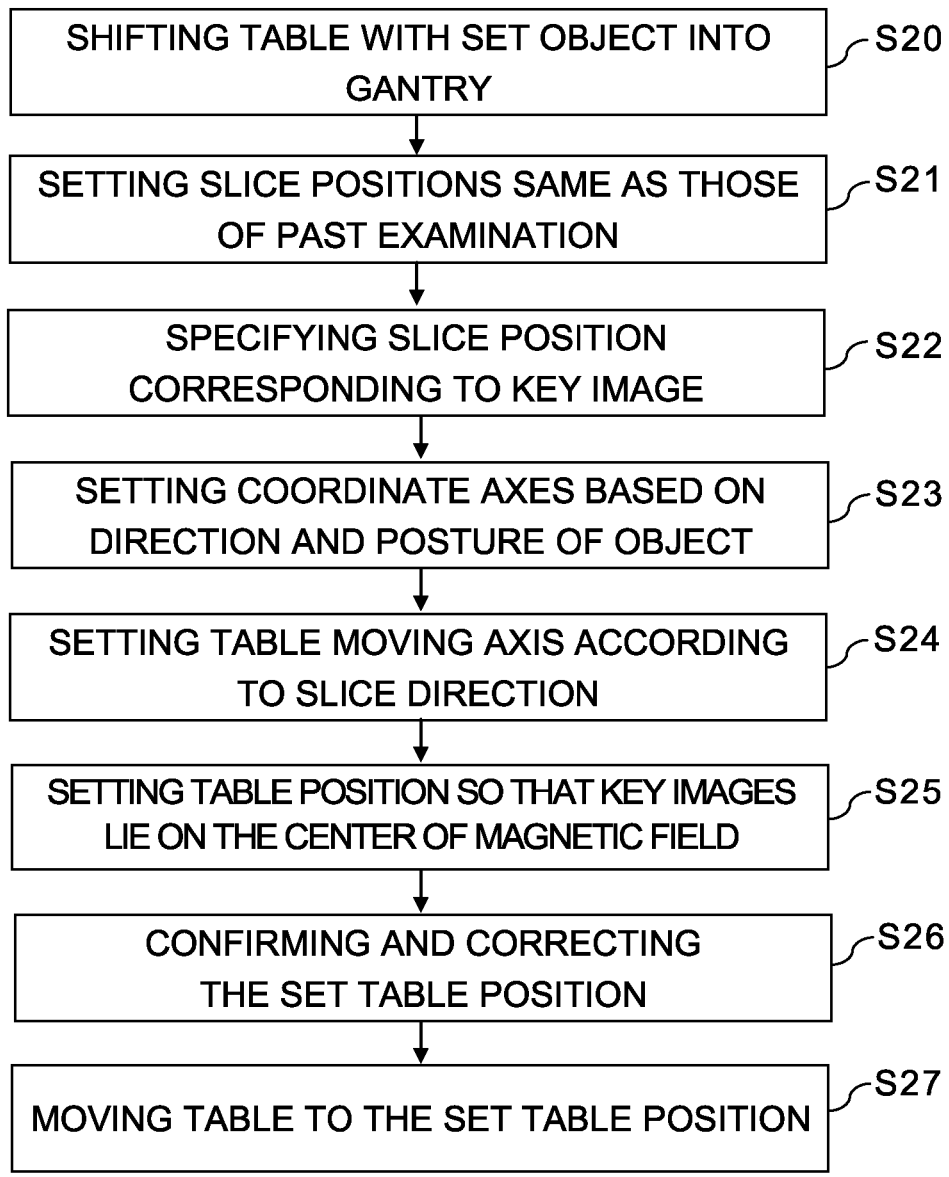
FIG. 4 is a flowchart showing a detailed flow for the set of the imaging conditions, including the same slice positions of which the key images lie on the center of magnetic field, shown in the step S15 of FIG. 3.

FIG. 4 is a flowchart showing a detailed flow for the set of the imaging conditions, including the same slice positions of which the key images lie on the center of magnetic field, shown in the step S15 of FIG. 3.

Firstly, in the step S20, the bed driving unit 37B drives and the table 37A with the set object P is shifted in the gantry. Then, positioning image data of the object P is acquired.

Next, in the step S21, the imaging position acquisition part 41A of the imaging condition setting unit 41 refers to the past object data and acquires the positioning image data and positions of respective slices set for the positioning image data. Then, the imaging condition setting unit 41 refers to the positions of the respective slices set for the past positioning image data and sets the same slice positions in the body coordinate system of the object P as an imaging condition for the reexamination.

Next, in the step S22, the interest image specifying part 41B of the imaging condition setting unit 41 acquires the key image information, including the marking information of the key images, the slice positions of the key images and the distances from the center of magnetic field to the key images, from the past object data. Subsequently, the interest image specifying part 41B specifies slice positions, corresponding to the key images among the slice positions acquired in the imaging position acquisition part 41A, in the body coordinate system.

Note that, the interest image specifying part 41B may acquire the key image information attached to the slice image data instead of the object data. In that case, if the interest image specifying part 41B is configured to refer to the report information generated in the medical image display apparatus 52, it becomes easy to acquire an address, at which the key image data is stored, by using a link, to the key image data, provided to the report information. Therefore, it is possible to perform search processing smoothly.

When the key image information are not attached to the past object data and the frames of slice image data in the past, a frame or frames of slice image data of interest can be designated as the key image data from the past frames of slice image data by the interest image specifying part 41B. Specifically, the key image data can be designated manually by inputting designating information of key images from the input device 33 to the interest image specifying part 41B. Alternatively, the interest image specifying part 41B may automatically designate slice image data with a ROI set as the key image data based on setting information of the ROI recorded in the past object data as vector information.

In this case, slice positions of the key image data designated by the interest image specifying part 41B are specified.

Next, in the step S23, the bed position setting part 41C sets a direction of the body coordinate system in the apparatus coordinate system based on a direction and a posture of the object P. As described above, the apparatus coordinate system can be set by defining the central axis direction of the static field magnet 21 as the z-axis, the horizontal direction orthogonal to the central axis of the static field magnet 21 as the x-axis, the vertical direction as the y-axis, and the origin (x, y, z)=(0, 0, 0) as the center of magnetic field.

Therefore, the body axis direction Zb of the object P in the body coordinate system points the z-axis of the apparatus coordinate system or the opposite direction of the z-axis according to a direction of the object P in the longitudinal direction of the table 37A which is the sending direction of the table 37A into the gantry. Accordingly, the positive and negative signs ± indicating the direction of the body axis direction Zb in the apparatus coordinate system are determined according to the direction of the object P in the longitudinal direction of the table 37A.

Furthermore, the axial direction, the coronal direction and the sagittal direction of the object P change according to a posture of the object P set on the table 37, i.e., whether the object P is supine, prone, sideways or the like. Accordingly, the relative directional relationship between the apparatus coordinate system and each of the axial direction, the coronal direction and the sagittal direction, according to the posture of the object P is determined.

For example, when the object P is set sideways on the table 37A, the sagittal direction perpendicular to the sagittal section becomes the y-axis direction of the apparatus coordinate system and the coronal direction perpendicular to the coronal section becomes the x-axis direction of the apparatus coordinate system. With the setting of the coordinate system as described above, it becomes possible to set the position of the table 37A according to the direction and the posture of the object P with respect to the table 37A.

Next, in the step S24, the bed position setting part 41C sets the shifting axis of the table 37A corresponding to the slice direction. Specifically, the shifting axis of the table 37 is set to the direction perpendicular to the key images and the slices.

For example, when the key images are sagittal section images and sagittal sections are set as slices with respect to the object P set supine on the table 37A, the shifting direction of the table 37A in order to set the positions of the key images to the center of magnetic field becomes the right and left direction of the object P. Specifically, the shifting direction of the table 37A becomes the horizontal direction orthogonal to the longitudinal direction of the table 37A. Therefore, the shifting axis of the table 37A is set to the x-axis of the apparatus coordinate system.

On the other hand, when the key images are coronal section images and coronal sections are set as slices with respect to the object P set supine on table 37A, the shifting direction of the table 37A in order to set the positions of the key images to the center of magnetic field becomes the up-and-down direction of the table 37A. Therefore, the shifting axis of the table 37A is set to the y-axis of the apparatus coordinate system.

Alternatively, when the key images are the axial section images and axial sections are set as slices with respect to the object P set supine on table 37A, the shifting direction of the table 37A in order to set the positions of the key images to the center of magnetic field becomes the longitudinal direction of the table 37A. Therefore, the shifting axis of the table 37A is set to the z-axis of the apparatus coordinate system.

Further, even if the key images are sagittal section images and sagittal sections are set as slices, the shifting direction of the table 37A in order to set the positions of the key images to the center of magnetic field becomes the up-and-down direction as long as the object P is set sideways on the table 37A. Therefore, the shifting axis of the table 37A is set to the y-axis of the apparatus coordinate system.

Similarly, if the key images and slices are coronal sections in the case where the object P is set sideways on the table 37A, the shifting axis of the table 37A is set to the x-axis of the apparatus coordinate system. Meanwhile, if the key images and slices are axial sections, the shifting axis of the table 37A is set to the z-axis of the apparatus coordinate system.

As described above, the shifting axis of the table 37A with consideration of the positive and negative signs can be set in the y-axis direction of the apparatus coordinate system which is up-and-down direction of the table 37A and the x-axis direction of the apparatus coordinate system which is the horizontal direction perpendicular to the longitudinal direction of the table 37A as well as the z-axis direction of the apparatus coordinate system which is the sending direction of the table 37A into the gantry. Herewith, it becomes possible to set the position of the table 37A in the longitudinal direction, the up-and-down direction or the horizontal direction orthogonal to the longitudinal direction of the table 37A according to a slice direction of slice positions.

Next, in the step S25, the bed position setting part 41C obtains the position of the table 37A in the apparatus coordinate system when the slice positions of the key images lie on the closest positions to the center of magnetic field. The position of the table 37A can be obtained based on the distances from the center of magnetic field to the slice positions corresponding to the key images.

When plural slice positions corresponding to the key images are set, the position of the table 37A in the apparatus coordinate system is obtained so that the representative position, such as the center or the gravity center of the slice positions, or the range covering the slice positions lies on the closest position to the center of magnetic field. Furthermore, when the slice position or positions corresponding to the key image or images are a section or sections, of which the normal direction is not a movable direction of the table 37A, like oblique sections, the position of the table 37A in the apparatus coordinate system is obtained so that the slice position corresponding to the key image or the representative position of the slice positions corresponding to the key images lies the closest position to the center of magnetic field, e.g., the position passing through the center of magnetic field.

Firstly, an example case of obtaining the position of the table 37A in the apparatus coordinate system so as to set a single slice position, corresponding to a single key image, to the center of magnetic field will be described.

Figure 5:
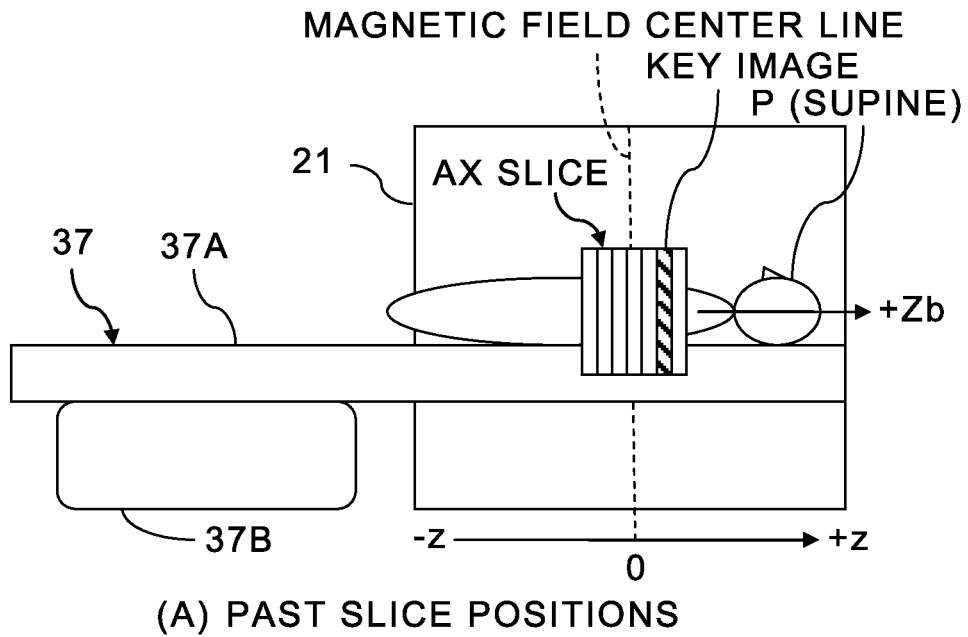
FIG. 5 is a view to explain a method for setting a position of the table in a case where a slice position of an axial key image set for a supine object is positioned on the center of the magnetic field, in the step S25 of FIG. 4.
Figure 5:
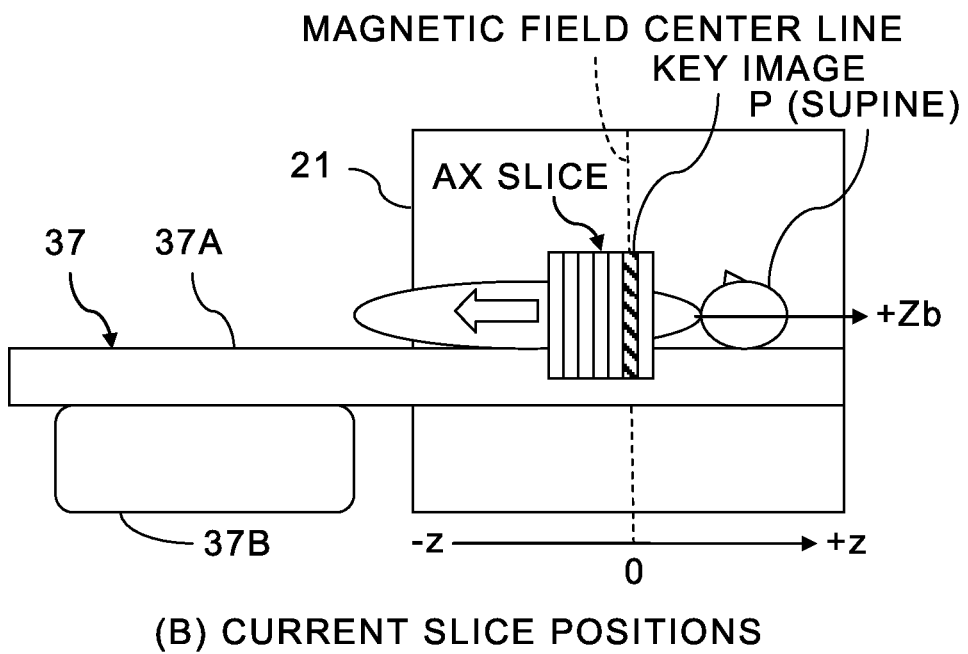

FIG. 5 is a view to explain a method for setting a position of the table 37A in a case where a slice position of an axial key image set for a supine object P is positioned on the center of the magnetic field, in the step S25 of FIG. 4.

FIG. 5 (A) is a view showing slice positions set in the past and FIG. 5 (B) is a view showing a state of the table 37A positioned so that the slice position of the key image becomes the center of magnetic field. Note that, the same applies for (A) and (B) indicated in the following figures.

As shown in FIG. 5 (A), the central axis direction of the static field magnet 21 can be set as the z-axis of the apparatus coordinate system and the center of magnetic field can be set as the origin z=0 of the apparatus coordinate system. Furthermore, the sending direction of the table 37A into the gantry can be set as the positive direction and the direction for sending out the table 37A from the gantry can be set as the negative direction.

As shown in FIG. 5 (A), when the body axis direction Zb is the +z-axis direction and slice positions in the axial direction have been set with respect to an object P set supinely in the past examination, imaging is generally performed in a state that the table 37A has been positioned so that the center of the slice positions becomes the center of magnetic field. Therefore, the slice positions of the key images of interest do not always become the center of magnetic field.

Accordingly, the position of the table 37A is shifted in the z-direction so that the slice position of the key image becomes the center of magnetic field, in the reexamination, as shown in FIG. 5 (B). For example, when slice positions in the range of −5 cm z+5 cm in the apparatus coordinate system have been imaged in the past examination and the slice position of the key image was z=2 cm, the position of the table 37A is set so that the slice position of the key image becomes z=0.

In the case where the default position of the table 37A has been set so that the center of slice positions to be imaging targets becomes the center of magnetic field, once in the present reexamination, the position of the object P in the apparatus coordinate system becomes the same as that of the object P in the past examination. Therefore, the position of the table 37A shifted by −2 cm toward the z-axis direction is set so that the slice position of the key image lying at z=2 cm becomes the center of magnetic field.

On the other hand, if the default position of the table 37A differs from the position of the table 37A in the past examination, the position of the object P in the apparatus coordinate system is different from the position of the object P in the past examination. Accordingly, the moving distance of the table 37A is calculated according to the relative distance between the body coordinate system and the apparatus coordinate system.

For example, in the case where the slice positions set on the same positions as those in the past in the body coordinate system have lied in the range of −4 cm≤z≤+6 cm in the apparatus coordinate system, the slice position of the key image lies at z=3 cm. Therefore, the position of the table 37A shifted by −3 cm toward the z-axis direction is set so that the slice position of the key image lying on z=3 cm at the default position of the table 37A becomes the center of magnetic field.

Figure 6:
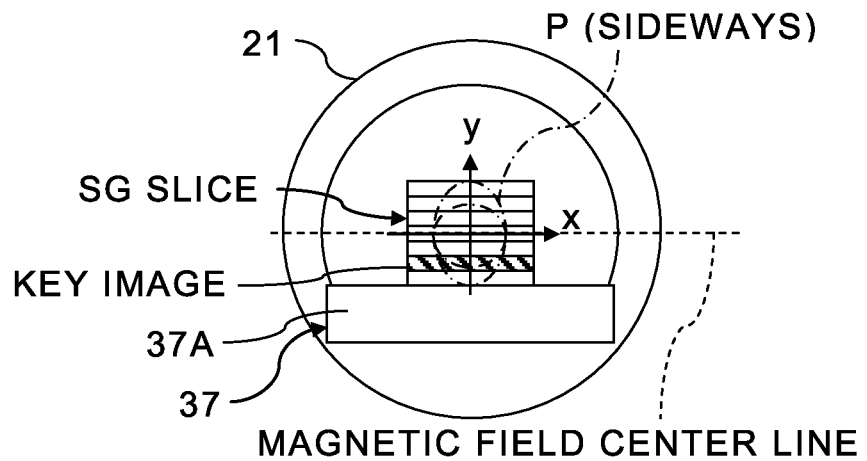
FIG. 6 is a view to explain a method for setting a position of the table in a case where a slice position of a sagittal key image set for a sideways object is positioned on the center of the magnetic field, in the step S25 of FIG. 4.
Figure 6:
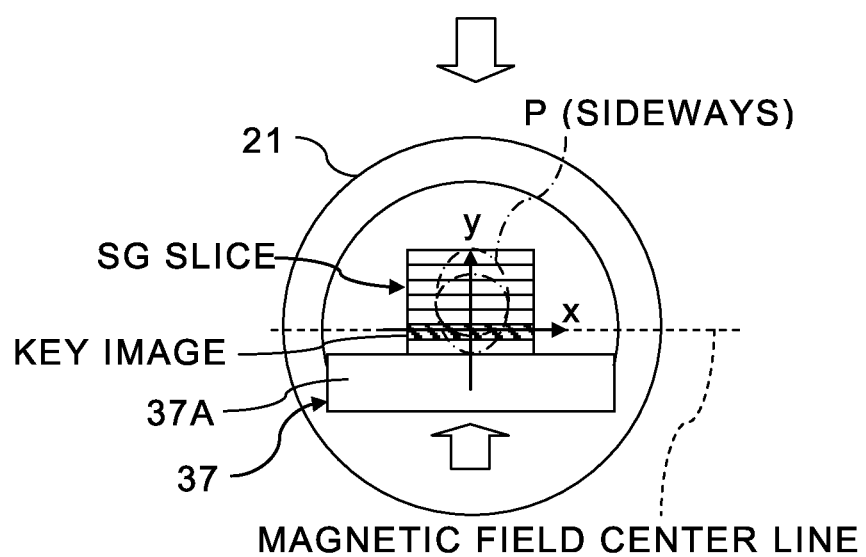

FIG. 6 is a view to explain a method for setting a position of the table 37A in a case where a slice position of a sagittal key image set for a sideways object P is positioned on the center of the magnetic field, in the step S25 of FIG. 4.

As shown in FIG. 6, the vertical direction can be defined as the y-axis of the apparatus coordinate system, the horizontal direction orthogonal to the central axis of the static field magnet 21 can be defined as the x-axis of the apparatus coordinate system and the center of magnetic field can be defined as the origin (x, y)=(0, 0) of the apparatus coordinate system.

As shown in FIG. 6 (A), in the case where the slice positions in the sagittal direction have been set with respect to the object P set sideways in the past examination, imaging is not always performed with the slice position of the key image of interest positioned on the center of magnetic field.

Accordingly, the default position of the table 37A shifted in the y-direction can be set in the reexamination as shown in FIG. 6 (B) by shifting the table 37A up and down so that the slice position of the key image becomes the center of magnetic field.

Next, the position setting of the table 37A in order to set plural slice positions corresponding to key images to the center of magnetic field will be described.

Figure 7:
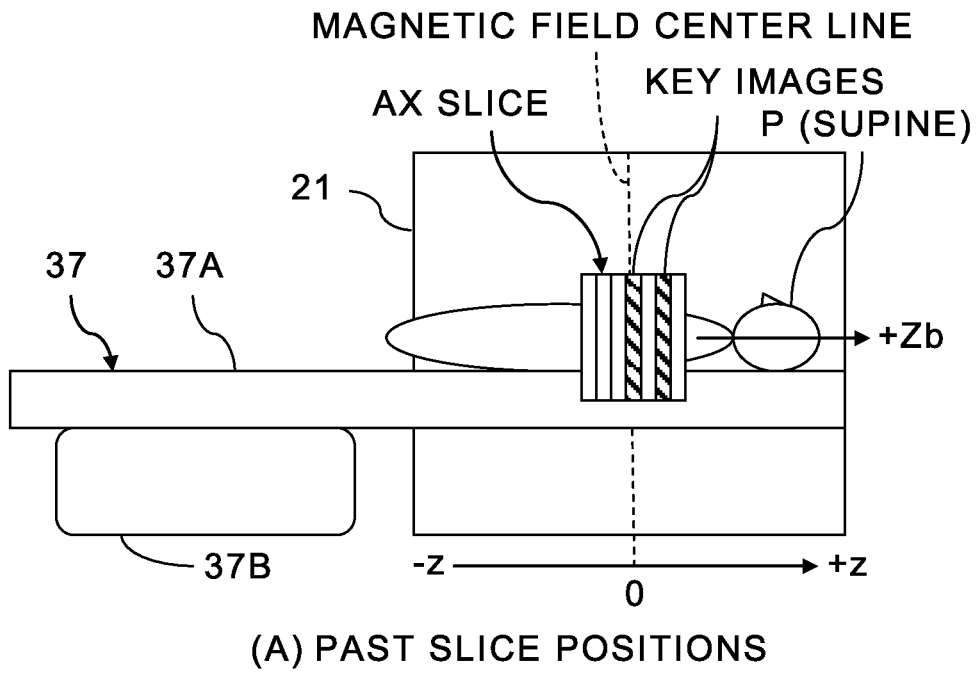
FIG. 7 is a view to explain the first method for setting a position of the table in a case where plural slice positions of axial key images set for an object are positioned on the center of the magnetic field, in the step S25 of FIG. 4.
Figure 7:
Figure 7:
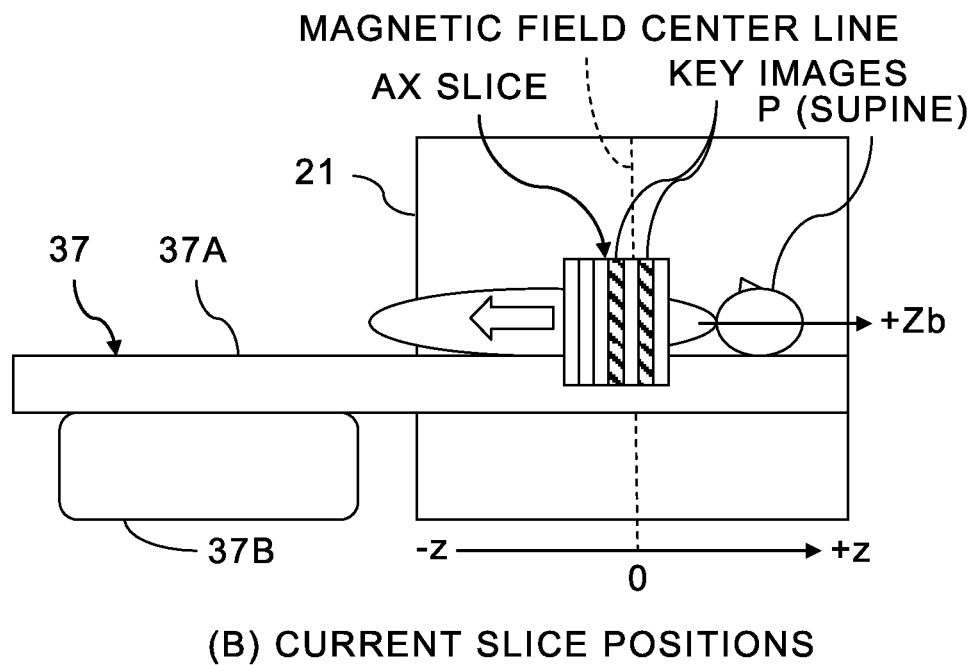

FIG. 7 is a view to explain the first method for setting a position of the table 37A in a case where plural slice positions of axial key images set for an object P are positioned on the center of the magnetic field, in the step S25 of FIG. 4.

As shown in FIG. 7 (A), when the slice positions designated among the slice positions as the key images have been set separately at both sides of another slice position, the position of the table 37A can be set so that the center position of the slice positions designated as the key images becomes the center of magnetic field, as shown in FIG. 7 (B).

Note that, in a case where slice positions of key images have been set continuously without interposing any slice position, the table 37A can be also positioned similarly so that the center position of the slice positions of the key images at the both ends becomes the center of magnetic field.

Figure 8:
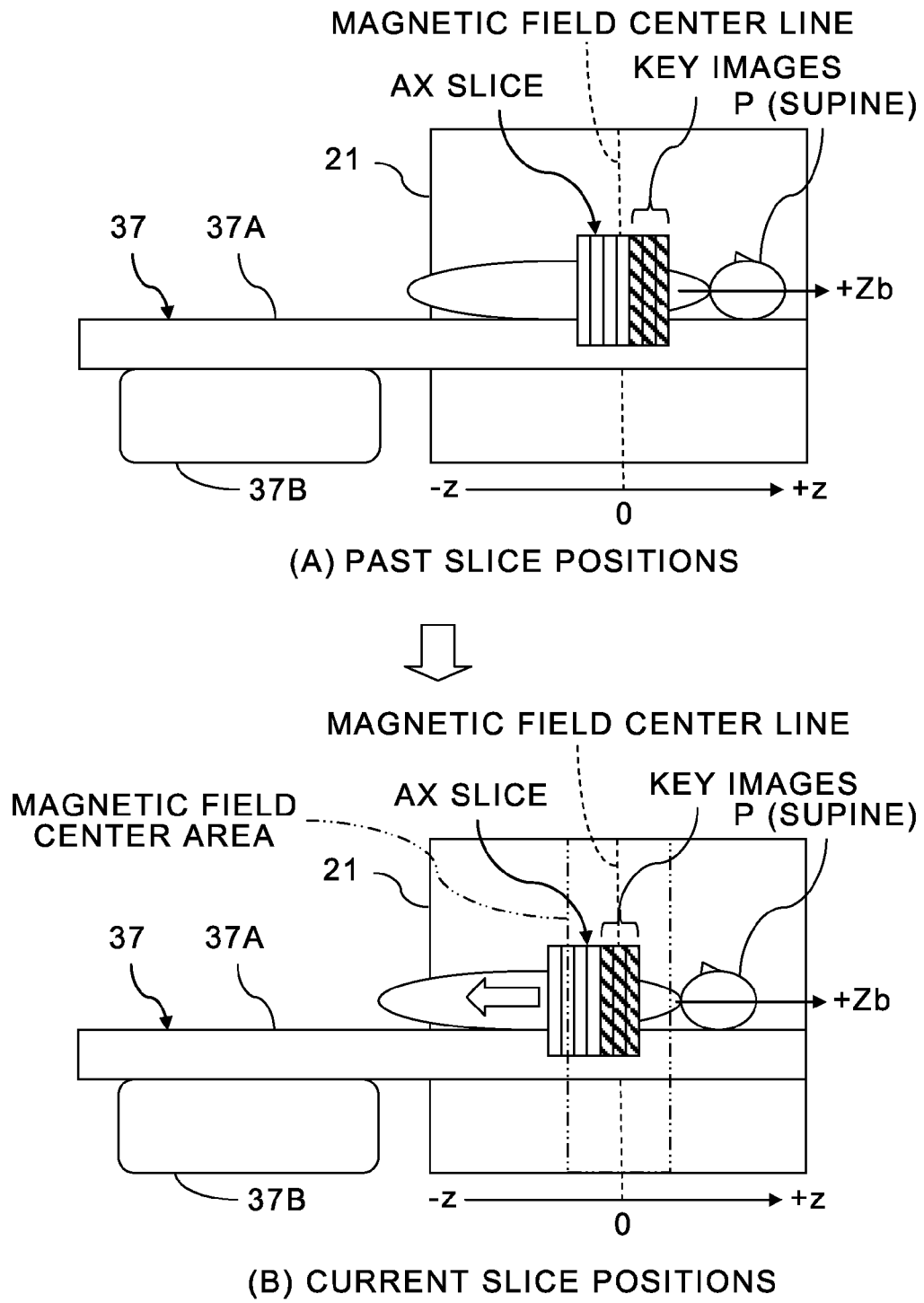
FIG. 8 is a view to explain the second method for setting a position of the table in a case where plural slice positions of axial key images set for an object are positioned on the center of the magnetic field, in the step S25 of FIG. 4.

FIG. 8 is a view to explain the second method for setting a position of the table 37A in a case where plural slice positions of axial key images set for an object P are positioned on the center of the magnetic field, in the step S25 of FIG. 4.

As shown in FIG. 8 (A), when a slice range of key images is set, the table 37A can be positioned so that the slice range of the key images lie on the center of magnetic field as a whole as shown in FIG. 8 (B). For that purpose, the table 37A can be positioned so that the slice range of the key images lies within a predetermined range from the center of magnetic field defined as a center area of magnetic field separately from a FOV. Alternatively, the table 37A can be positioned so that the slice range of the key images lies within the FOV. That is, the position of the table 37A can be set so that the slice range designated as the key images out of the slice positions becomes within a predetermined range, such as the FOV, from the center of magnetic field.

Furthermore, the bed position setting part 41C may automatically detect the center position or the end positions of a slice range of key images to position the table 37A so that the center position or one end position, which is automatically detected, becomes the center of magnetic field. Note that, when the center position of a slice range of key images is set to the center of magnetic field, the table 37A is positioned similarly to the example shown in FIG. 7.

Figure 9:
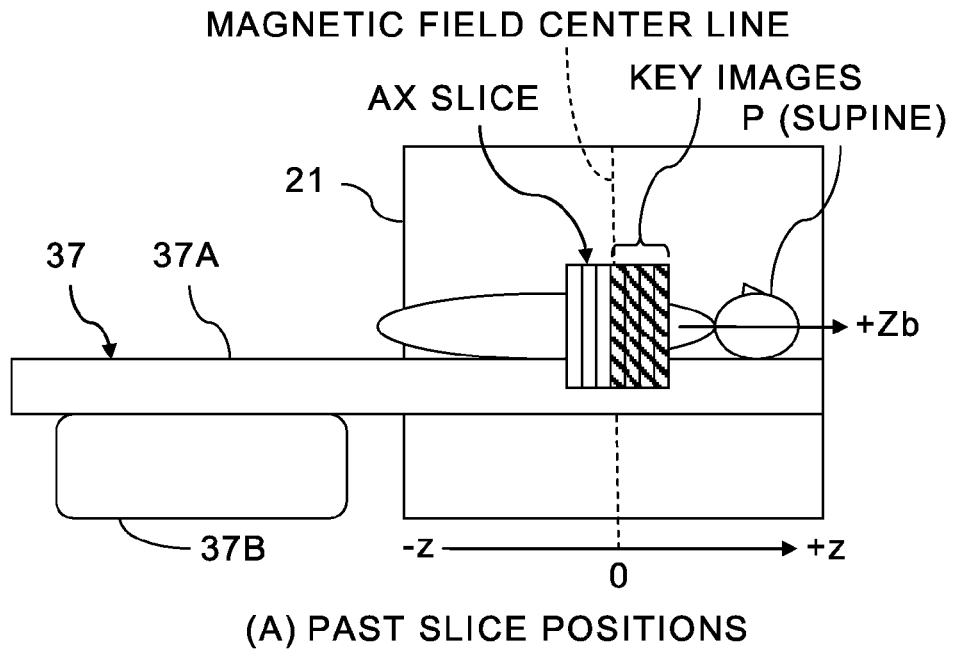
FIG. 9 is a view to explain the third method for setting a position of the table in a case where plural slice positions of axial key images set for an object are positioned on the center of the magnetic field, in the step S25 of FIG. 4.
Figure 9:
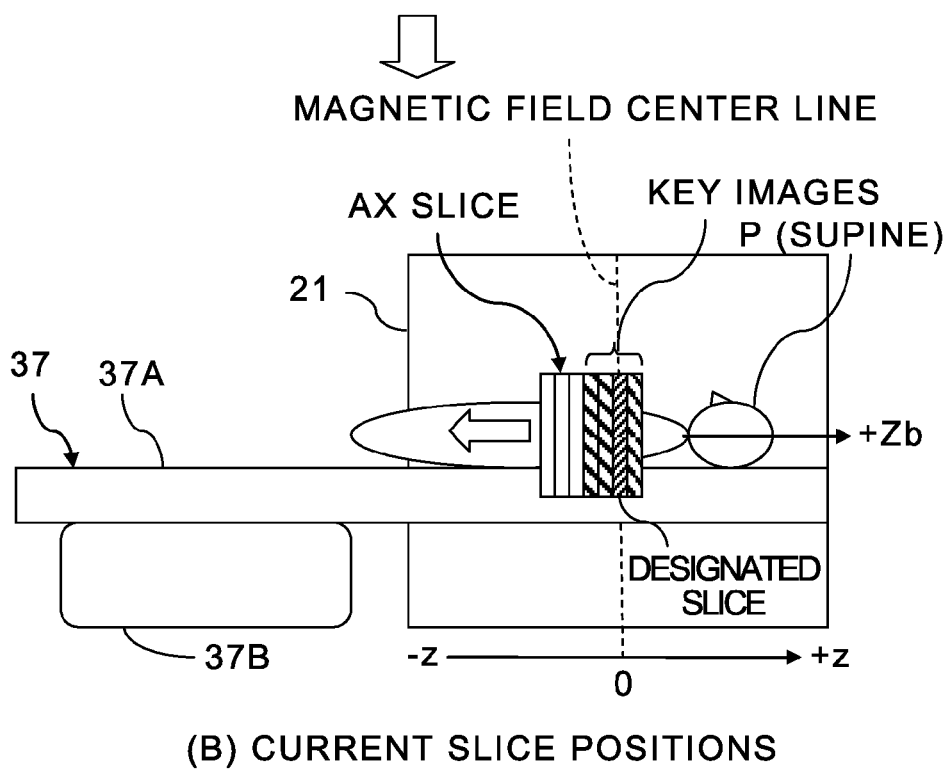

FIG. 9 is a view to explain the third method for setting a position of the table 37A in a case where plural slice positions of axial key images set for an object P are positioned on the center of the magnetic field, in the step S25 of FIG. 4.

As shown in FIG. 9 (A), when plural slice positions of key images are set, the table 37A can be positioned so that a slice position designated out of the slice positions of the key images lies on the center of magnetic field as shown in FIG. 9 (B). Specifically, the position of the table 37A can be set so that a single slice position further designated from the slice positions which have been designated as the key images out of the slice positions lies on the center of magnetic field.

The slice position to be on the center of magnetic field may be automatically determined by the bed position setting part 41C according to a predetermined algorithm or may be manually specified by the bed position setting part 41C according to designating information input from the input device 33.

Examples of the algorithm for automatically determining the slice position to be on the center of magnetic field include an algorithm in which the slice position of the central key image is set to the center of magnetic field when the number of the key images is odd while either one of the two slice positions nearest the center is set to the center of magnetic field when the number of the key images is even.

Furthermore, in the medical equipment group 39 such as the medical image processing apparatus 51, it is also possible to automatically or manually predesignate a slice position which should be set to the center of magnetic field out of the slice positions of the key images. In this case, a slice position to be the center of magnetic field can be attached as tag information of data, such as the object data and/or diagnostic image data, of the DICOM protocol. Then, the bed position setting part 41C can specify a single slice position, which should be the center of magnetic field, out of the slice positions of the key images, with reference to tag information of data of the DICOM protocol.

Figure 10:
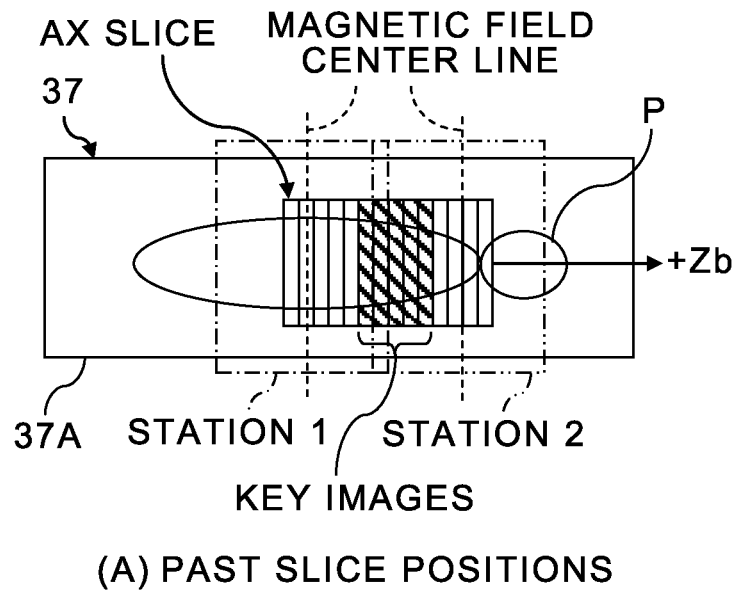
FIG. 10 is a view to explain a method for setting a position of the table in a case where slice positions of key images set in past imaging under the stepping-table method are positioned on the center of the magnetic field, in the step S25 of FIG. 4.
Figure 10:
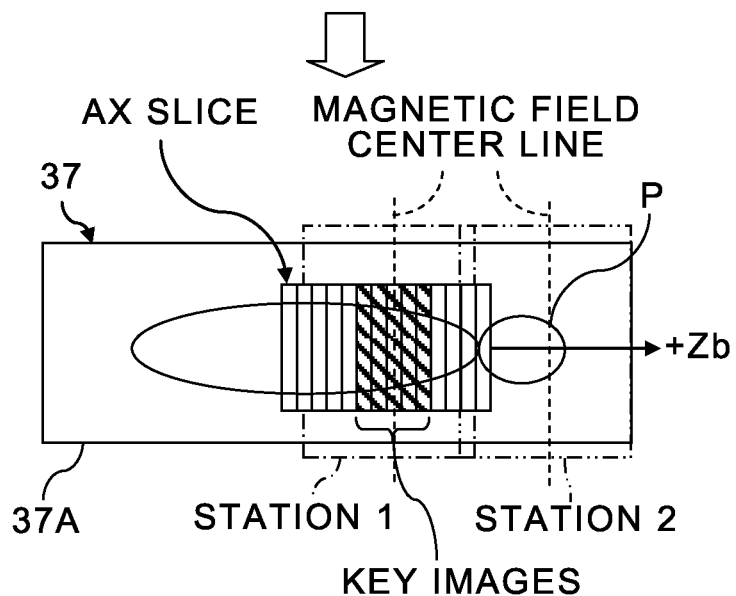

FIG. 10 is a view to explain a method for setting a position of the table 37A in a case where slice positions of key images set in past imaging under the stepping-table method are positioned on the center of the magnetic field, in the step S25 of FIG. 4.

When past imaging was performed by the stepping-table method, slice positions of axial sections are set so as to stride different station positions (station1, station2) as shown in FIG. 10 (A). Furthermore, when plural key images were set, the key images may stride different station positions (station1, station2). According to the example shown in FIG. 10 (A), the overlapped two station positions (station1, station2) have been set and five slice positions of key images have been set with straddling the two station positions (station1, station2).

Accordingly, as shown in FIG. 10 (B), it is possible to position the table 37A so that at least a slice position or slice positions corresponding to a key image or key images become the center of magnetic field at a common station position. In this case, it becomes possible to acquire the all key images at a common station position. Specifically, the position of the table 37A can be set so that slice positions designated as key images straddling mutually different positions of the table 37A, out of the slice positions set in the past accompanying a move of the table 37A, can be set at a common position of the table 37A.

As described above, it is possible to set the slice positions same as those in the past on a same object P and to set the table position of the bed 37 on which the object P has been set so that the representative position of designated slice positions out of the slice positions or the representative position of a designated slice range out of the slice positions becomes the center of magnetic field.

After the setting of the position of the table 37A as described above has been completed, next in the step S26, the bed position setting part 41C performs the confirmation and correction of the position of the table 37A which has been set so that the slice positions of the key images become the center of magnetic field.

When the position of the table 37A has been set so that the slice position of the key image becomes the center of magnetic field, a slice position other than the key image may be too far from the center of magnetic field. Furthermore, when the position of the table 37A has been set so that the respective slice positions of the key images become within a range around the center of magnetic field, not only the slice positions other than the key images but also some slice positions of the key images may be too far from the center of magnetic field. In such case, when imaging is performed at the set position of the table 37A without a move, image qualities in images corresponding to the slice positions distant from the center of magnetic field may be deteriorated.

Accordingly, the bed position setting part 41C displays the slice positions after setting the position of the table 37A on the display unit 34. Therefore, a user can visually confirm the distances of the slice positions from the center of magnetic field.

In addition, the bed position setting part 41C determines whether the slice positions after setting the position of the table 37A are within a predetermined range from the center of magnetic field or not. Then, when the slice positions, same as those in the past, after setting the position of the table 37A are out of the predetermined range from the center of magnetic field, the bed position setting part 41C shows information indicating that the slice positions same as those in the past are out of the predetermined range from the center of magnetic field. For example, warning information can be displayed on the display unit 34. Note that, the predetermined range serving as a criterion of the determination processing can be preliminarily determined as an experiential range which is considered to have no effect leading to degradation in image quality.

Furthermore, the bed position setting part 41C displays choices together with the warning information on the display unit 34. The choices can be arbitrary ones which can be selected by a user when the slice positions after setting the position of the table 37A become out of a predetermined range from the center of magnetic field.

For example, it is possible to prepare various choices such as: the first choice to perform imaging after moving table 37A to the position set so that slice positions of key images lie at the magnetic field center; the second choice to perform imaging after moving table 37A to the position where slice positions of key images are closest to the center of magnetic field center while keeping the slice positions within a predetermined range from the magnetic field center; the third choice to perform imaging after adjusting the position of the table 37A manually by inputting instructing information to the bed position setting part 41C from the input device 33; and the fourth choice to perform imaging at the default position of the table 37A without moving the table 37A.

Furthermore, when slice positions designated as key images are out of a predetermined range from the center of magnetic field as a result of setting the position of the table 37A so that a slice position further designated from the slice positions which are designated as the key images becomes the center of magnetic field, it is possible to prepare a choice for setting again the position of the table 37A so that the slice positions designated as the key images become within a predetermined range from the center of magnetic field.

Then, by inputting select information of a choice as instructing information from the input device 33 to the bed position setting part 41C, it is possible to correct the control position of the table 37A by the bed position setting part 41C. Specifically, it is possible to set again the position of the table 37A according to the instructing information input from the input device 33 as a response to the information showing that the slice positions same as those in the past are not within a predetermined range from the center of magnetic field.

For example, by selecting the second choice with an operation of the input device 33, imaging can be performed after moving the table 37 A to the optimum position for the all slice positions to be imaging targets. As a concrete example, when a predetermined range from the center of magnetic field within which an influence of disturbance of image quality due to the ununiformity in the magnetic field is acceptable is ±20 cm from the center of magnetic field, a position of the table 37A at which the all slice positions are within ±20 cm from the center of magnetic field and the slice positions of the key images are the closest to the center of magnetic field is set to an adjusted control position of the table 37A.

Next, in the step S27, the table 37A is moved to the appropriate control position of the table 37A set on the basis of the distances from the center of magnetic field to the slice positions of the key images, the all slice positions which are the imaging targets and the predetermined distance from the center of magnetic field at which the influence of disturbance of image quality due to ununiformity in the magnetic field is acceptable.

Specifically, the imaging condition setting unit 41 outputs the control position of the table 37A to the bed driving unit 37B through the sequence controller 31. Then, the bed driving unit 37B moves the table 37A to the control position according to the positioning information of the table 37A input as a control signal from the sequence controller 31. Herewith, the table 37A is positioned to an appropriate position for which the distances from the center of magnetic field to the slice positions including the slice positions of the key images are considered.

Next, in the step S16 of FIG. 3, imaging is performed again at the moved position of the table 37A in a flow similar to that for the imaging in the step S4. Specifically, MR data is acquired from the slice positions set to the object P at the table position of the bed 37 and image data corresponding to the slice positions is generated based on the acquired MR data. Herewith, slice image data including the key image data corresponding to the reexamination is acquired and it is possible to display the slice image data on the display unit 34 and store the slice image data in the image data storage unit 46.

Next, in the step S17, the object data of the DICOM protocol which is made by attaching the key image information, the image processing condition information and the imaging conditions including the respective slice positions with the positioning image data used to set the imaging conditions for the re-imaging is generated in the reference information production unit 43 similar to the step S5.

Next, in the step S18, the communication unit 44 transmits the set of the slice image data acquired by the re-imaging and the correspondent object data to the medical image server 50 through the network 40 similar to the step S6.

Next, in the step S19, the slice image data and the object data, corresponding to the reexamination, transmitted from the communication unit 44 of the magnetic resonance imaging apparatus 20 are stored in the medical image server 50. Then, a user can display the slice image data, corresponding to a past examination, stored in the medical image server 50 and the slice image data acquired by the reexamination with using a medical equipment such as the medical image display apparatus 52 or the medical image processing apparatus 51 to make a diagnostic report by a comparative interpretation.

In this case, the key image data of interest has been generated based on NMR signals acquired at a position close to the center of magnetic field in the reexamination. Therefore, it is possible to observe key images of interest as images each having an improved image quality.

In addition, it is possible to perform a reexamination repeatedly with setting slice positions of key images to positions close to the center of magnetic field in a flow similar to that shown from the step S10 to the step S19. In this case, once slice positions of key images are fixed, it becomes possible to acquire and display key image data with an improved image quality constantly.

That is, the above-mentioned magnetic resonance imaging apparatus 20 is an apparatus configured to be able to automatically set a position of the table 37A so that slice positions corresponding to key images designated as images of interest become close to the center of magnetic field in case of repeatedly imaging slice positions set to a same object P Therefore, according to the magnetic resonance imaging apparatus 20, it is possible to generate image data, at slice positions involving a target part of interest, based on NMR signals acquired at the center of magnetic field or positions close to the center of magnetic field in case of setting the same slice positions as those in the past to perform a reexamination of a same object P. Consequently, it is possible to acquire slice image data of high interest with an improved image quality and to obtain a set of slice image data which can be compared with a past multi slice image data group.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

For example, a case of imaging repeatedly by the same magnetic resonance imaging apparatus 20 has been described in the above-mentioned example. However, the slice positions same as those set in the past in another magnetic resonance imaging apparatus or an image diagnostic apparatus, such as a PET apparatus, other than a magnetic resonance imaging apparatus can be set in the magnetic resonance imaging apparatus 20.

What is claimed is:

1. A magnetic resonance imaging (MRI) apparatus comprising:
    MRI system components including static and gradient magnetic field generators, at least one radio frequency (RF) coil, RF transmitter and receiver circuits and at least one computer configured to control said components to effect
    for a patient to be imaged, setting a table position of a patient bed so that at least one imaging slice position, out of slice positions set for the patient to be imaged, is located at a center of the static magnetic field, said at least one imaging slice corresponding to at least one key slice previously imaged in a past examination of the patient to be imaged;
    determining whether the at least one set imaging slice position(s) is(are) within a predetermined range from the static magnetic field center; and
    if so, acquiring magnetic resonance data from the patient at the set table position(s) for the at least one slice position(s) to generate image data corresponding to the at least one slice position(s) based on the acquired magnetic resonance data.

2. The magnetic resonance imaging apparatus of claim 1, wherein the table position is set so as to locate center positions of key slice images on the center of the static magnetic field.

3. The magnetic resonance imaging apparatus of claim 1, wherein the table position is set so as to locate a range of slices, corresponding to the at least one key slice image, within the predetermined range from the center of the static magnetic field.

4. The magnetic resonance imaging apparatus of claim 1, wherein the table position is set so as to locate a slice position, designated from plural key image slice positions, on the center of the static magnetic field.

5. The magnetic resonance imaging apparatus of claim 4, wherein the table position is reset so as to locate slice positions corresponding to key image slices within the predetermined range from the center of the magnetic field when the slice positions of the key images are out of the predetermined range.

6. The magnetic resonance imaging apparatus of claim 1, wherein the at least one key previously imaged slice position is acquired as incidental information attached to image data of a transmission protocol for medical image data, the image data having been received through a network.

7. The magnetic resonance imaging apparatus of claim 6, wherein a distance from the center of the static magnetic field to the at least one position corresponding to the at least one key image is acquired as the incidental information, to set the table position based on the acquired distance from the center of the magnetic field.

8. The magnetic resonance imaging apparatus of claim 1, wherein the table position is set according to a direction and a posture of the patient with respect to a table.

9. The magnetic resonance imaging apparatus of claim 1, wherein the table position is set in a longitudinal direction of a table, an up-and-down direction of the table or a horizontal direction orthogonal to the longitudinal direction of the table, according to a slice direction of the slice positions.

10. The magnetic resonance imaging apparatus of claim 1, wherein information showing that the set slice positions are out of the predetermined range from the center of the static magnetic field is presented to an operator.

11. The magnetic resonance imaging apparatus of claim 10, wherein the table position is reset according to operator input instructing information as a response to the presented information showing that the currently set slice positions are out of the predetermined range.

12. The magnetic resonance imaging apparatus of claim 1, wherein slice positions are set to be the same as past slice positions set in an image diagnostic apparatus other than a magnetic resonance imaging apparatus.

13. The magnetic resonance imaging apparatus of claim 1, wherein the table position is set so as to allow key slice positions designated, out of past slice positions set with moving a table, to be settable at a common position of the table, the designated slice positions straddling mutually different positions of the table.

14. A magnetic resonance imaging (MRI) method comprising:
using an MRI system including static and gradient magnetic field generators, at least one radio frequency (RF) coil, RF transmitter and receiver circuits and at least one computer configured to control said components to effect
setting a table position of a patient bed to position at least one imaging slice position, out of slice positions set for a patient to be imaged, on a center of a static magnetic field, said at least one imaging slice corresponding to at least one key slice previously imaged in a past examination of the patient to be imaged;
determining whether the at least one set imaging slice position(s) is(are) within a predetermined range from the static magnetic field center; and
if so, acquiring magnetic resonance data from a patient at the slice positions set for the bed table position to generate image data.

15. A magnetic resonance imaging (MRI) apparatus comprising:
MRI system components including static and gradient magnetic field generators, at least one radio frequency (RF) coil, RF transmitter and receiver circuits and at least one computer configured to control said components to effect
setting a table position of a patient bed to position at least one slice image position, out of image slice positions set for a patient, at the static magnetic field center, said at least one slice image position corresponding to at least one key image of the patient acquired in a past examination; and
acquiring magnetic resonance data from set imaging slice positions for the patient at corresponding set bed table positions to generate image data,
wherein the table position is set in a sagittal direction of the patient.

16. A magnetic resonance imaging (MRI) apparatus comprising:
MRI system components including static and gradient magnetic field generators, at least one radio frequency (RF) coil, RF transmitter and receiver circuits and at least one computer configured to control said components to effect
setting a table position of a patient bed to position at least one slice image position, out of image slice positions set for a patient, at the static magnetic field center, said at least one slice image position corresponding to plural key images of the patient acquired in a past examination; and
acquiring magnetic resonance data from set imaging slice positions for the patient at corresponding set bed table positions to generate image data,
wherein the table position is set based on slice position information of the plural key images.

* * * * *